US006628807B1

United States Patent
Mumelter et al.

(10) Patent No.: US 6,628,807 B1
(45) Date of Patent: Sep. 30, 2003

(54) METHOD AND EQUIPMENT FOR TESTING THE COLOR AND REFLECTIVITY OF HIGH-VISIBILITY GARMENTS

(75) Inventors: Heinrich Mumelter, Bolzano (IT); Riccardo Bolognini, Massa Marittima (IT)

(73) Assignee: Lavanderie Dell'Alto Adige S.p.A., Ora (IT)

( * ) Notice: Subject to any disclaimer, the term of this patent is extended or adjusted under 35 U.S.C. 154(b) by 0 days.

(21) Appl. No.: 09/536,468

(22) Filed: Mar. 28, 2000

(51) Int. Cl.[7] .................................................. G06K 9/00
(52) U.S. Cl. .................... 382/111; 382/141; 356/237.1; 700/143
(58) Field of Search .................... 382/111, 141–145, 382/164, 165; 356/237.1, 238.2, 238.1, 238.3; 700/130, 131, 132, 133, 134, 135, 143; 33/2 R, 4, 5, 6, 17 A, 17 R

(56) References Cited

U.S. PATENT DOCUMENTS

| 3,942,154 A | * | 3/1976 | Akami et al. ................ 382/111 |
| 4,744,035 A | * | 5/1988 | Hashim ........................ 700/143 |
| 5,068,799 A | * | 11/1991 | Jarrett, Jr. ..................... 702/40 |
| 5,125,034 A | * | 6/1992 | Hudson et al. .............. 382/111 |
| 5,159,185 A | | 10/1992 | Lehr |
| 5,530,652 A | * | 6/1996 | Croyle et al. ............... 700/130 |
| 5,633,722 A | * | 5/1997 | Wasinger et al. ............ 356/402 |
| 5,751,834 A | * | 5/1998 | Lisk, Jr. ...................... 382/111 |
| 6,369,896 B1 | * | 4/2002 | Castello et al. .............. 356/430 |
| 6,373,979 B1 | * | 4/2002 | Wang .......................... 382/165 |

FOREIGN PATENT DOCUMENTS

| WO | WO91/16619 | 10/1991 |
| WO | WO92/03721 | 3/1992 |
| WO | WO98/36258 | 8/1998 |

OTHER PUBLICATIONS

Database WPI, Section Ch, Week 9118, Derwent Publications Ltd., London, GB, XP–002096576.
Database WPI Section Ch, Week 9118, XP002096576 & JP 03 070600 A Kurosawa, Mar. 26, 1991, Abstract.

* cited by examiner

*Primary Examiner*—Amelia M. Au
*Assistant Examiner*—Anand Bhatnagar
(74) *Attorney, Agent, or Firm*—Arent Fox Kintner Plotkin & Kahn

(57) ABSTRACT

A device for testing the color and reflectivity of garments by obtaining a image of the garment to be tested and reference samples simultaneously and segmenting the image of the garment into zones and obtaining characteristics, i.e. color, reflectivity, and brightness, of the each zone which are compared to the reference samples. The zones are then displayed where the zones that are within range are displayed in one color and those out of the range are displayed in another color.

6 Claims, 3 Drawing Sheets

Tav. 1

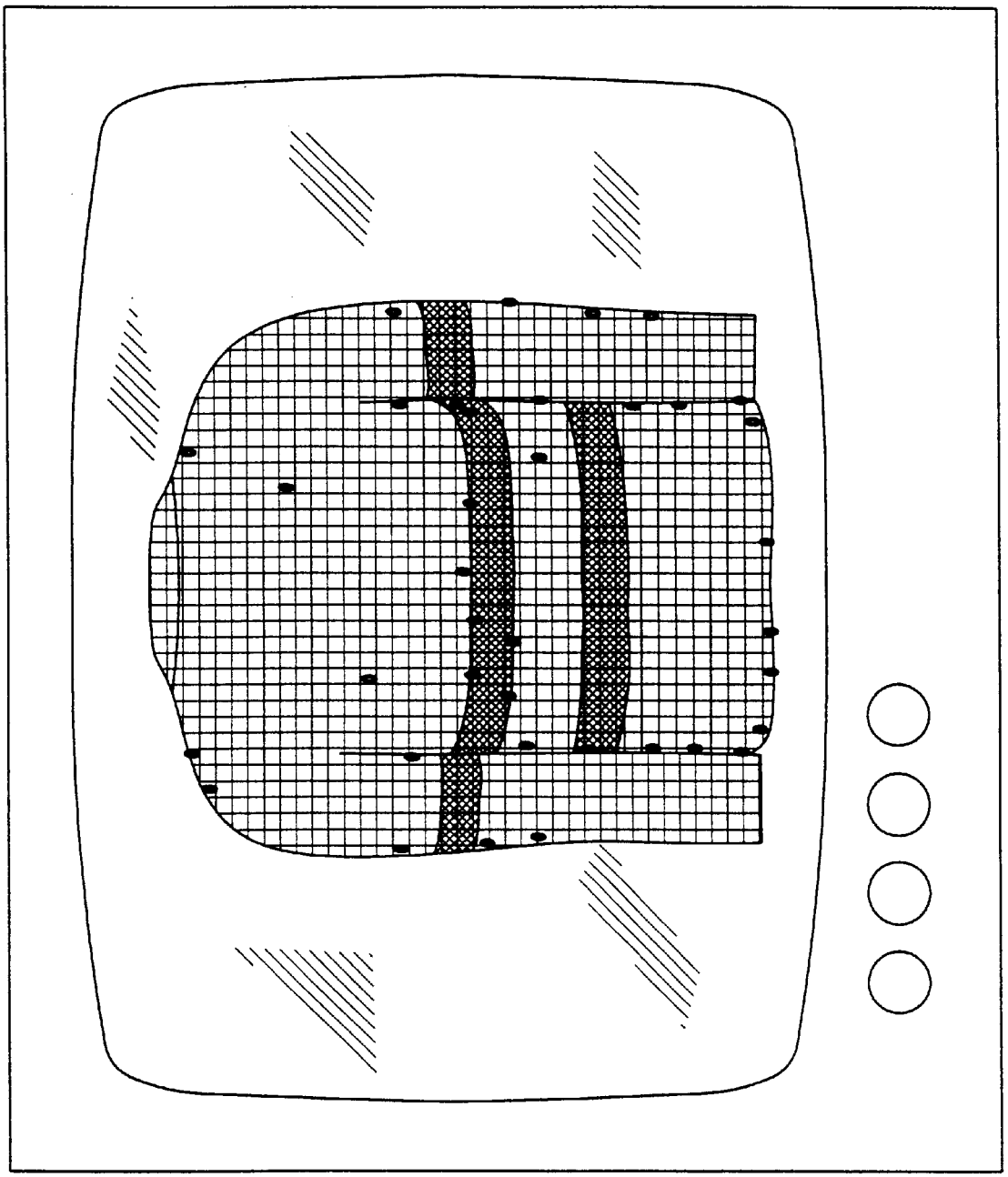

METHOD AND EQUIPMENT FOR TESTING THE COLOR AND REFLECTIVITY OF HIGH-VISIBILITY GARMENTS

BACKGROUND AND SUMMARY OF THE INVENTION

This invention relates to a method and the corresponding equipment for testing the colour and reflectivity characteristics of high-visibility garments, in order to establish whether they conform to industry standards.

The method in accordance with the invention involves the simultaneous acquisition of a digitalised image of the garment to be analysed and a reference sample by the same equipment, breakdown of the surface of the garment into a number of zones and measurement of the colour and reflectivity characteristics of each zone;

comparison of each measurement thus taken with the same measurement relating to the reference sample;

display of an image of the garment in which the zones presenting colour and/or reflectivity characteristics that fail to comply with the required limits are displayed in a different colour.

The patent also relates to the equipment designed to implement the said method.

The method in accordance with the invention enables garments to be tested quickly and precisely by a fully automatic process which offers the advantages of a considerable saving of time and precise, immediately displayed results.

The method and equipment in accordance with the invention are particularly suitable for use in the field of manufacture and treatment (washing, etc.) of high-visibility garments, such as working clothes of the type used at roadworks, where the workers need to be visible from a distance even in poor lighting conditions.

For this purpose, garments of a colour easily visible from a distance (generally orange or similar) are used, and a number of bands covered with a material that reflects nearly all the light received are applied to them.

As already mentioned, these garments are particularly useful in all cases in which workers have to operate in difficult and/or dangerous situations; they are used, for example, by rescue teams, personnel who work at night or in conditions of poor visibility on sites where moving vehicles are present, etc.

To meet the current regulations, these garments must present precise characteristics relating to the shade of colour and degree of reflectivity of the materials used; these characteristics must be checked periodically, in particular after washing operations and the like.

Until a few years ago, this type of check was performed empirically by placing the garment next to a set of colour samples, one of which, corresponding to the standard, was taken as the main reference, while the others departed from the optimum value to a greater or lesser extent.

The evaluation consists of a visual inspection designed to establish which of these samples is most similar to the colour of the garment; however, this method involves a degree of uncertainty and the risk of error, caused for example, by different lighting conditions, operator evaluation errors, etc.

Instrumental reading methods were recently introduced which involve the use of an instrument able to read the colour, reflectivity and brightness values of a small area of fabric and compare them with a table of preset values.

However, this is a merely a spot reading, ie. it relates only to one spot or a very small area of the garment, with the result that numerous readings are required; calculation and interpolation techniques are then used to obtain information about the whole surface, but the method does not guarantee that the results in each of these areas comply with the standard.

The present invention falls into this sector; its purpose is to provide a rapid, simple instrumental method of checking the whole surface of a garment which produces precise, reliable results that are easily and immediately interpreted.

This purpose is achieved with the method and equipment in accordance with the characterising part of the claims annexed hereto.

This invention will now be described in detail, by way of example but not of limitation, by reference to the annexed figures in which:

BRIEF DESCRIPTION OF THE DRAWINGS

FIG. 3 illustrates the image that appears on the screen which displays the readings taken.

DETAILED DESCRIPTION OF THE PREFERRED EMBODIMENT

Figure 1:
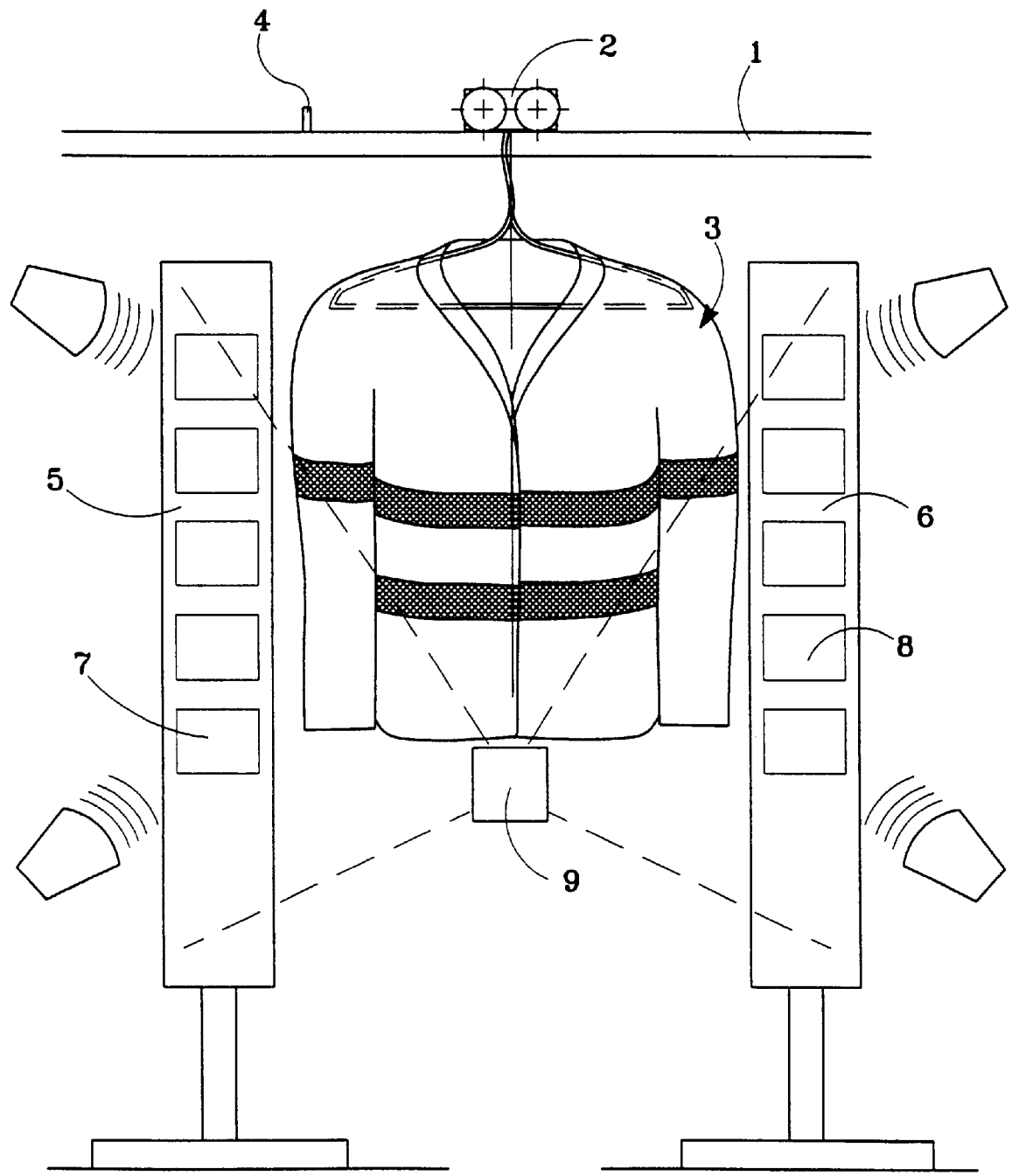
FIG. 1 schematically illustrates a unit in accordance with the invention, designed to test the colour and reflectivity of high-visibility garments
Figure 2:
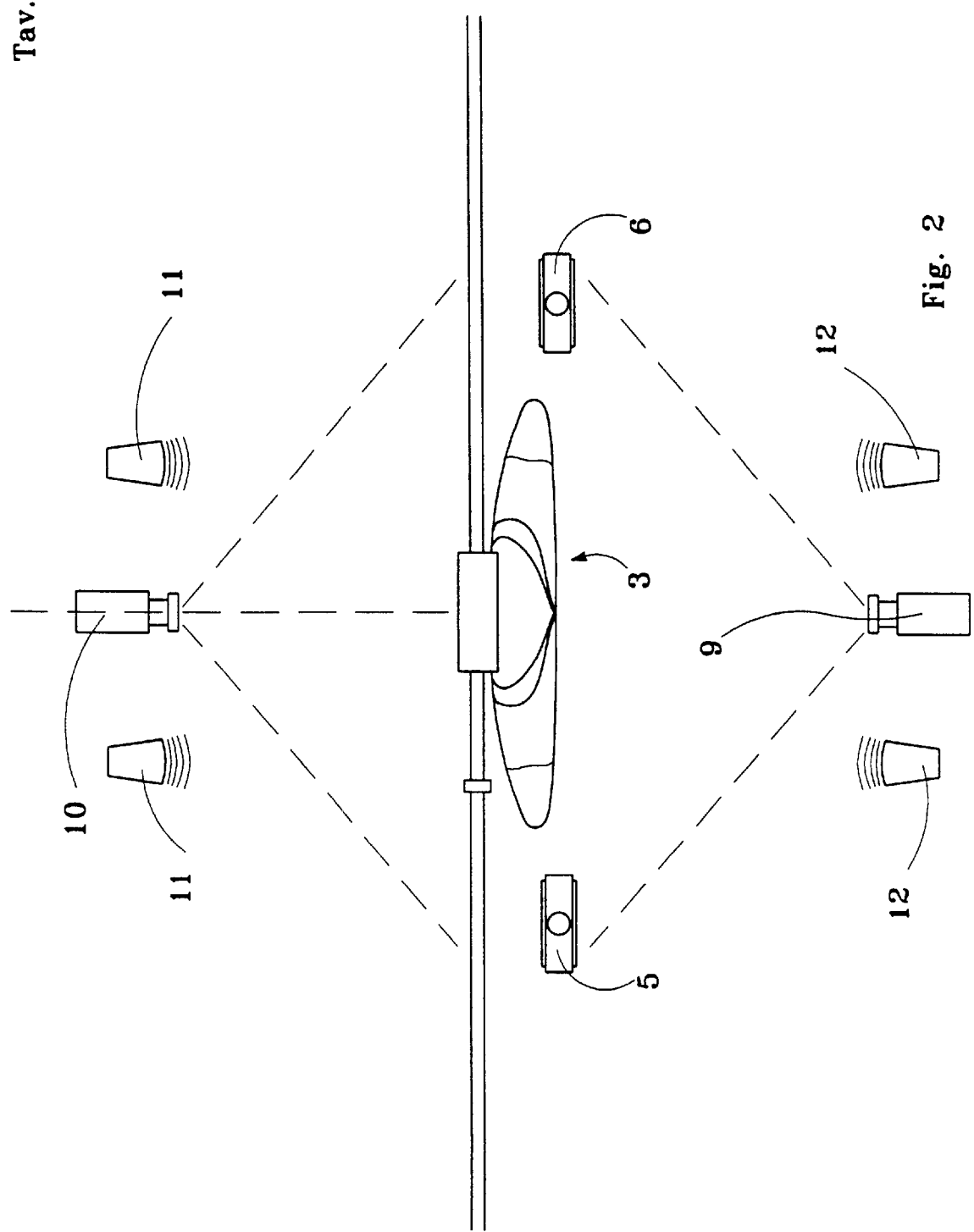
FIG. 2 is a schematic plan view of the test unit shown in FIG. 1

With reference to FIGS. 1 and 2, the unit designed to implement the method in accordance with the invention comprises a track or guide 1 along which set of carriages 2 run; a garment to be tested, indicated as 3, hangs from each carriage.

Along the route followed by the carriage, the garments pass through a test zone in which the carriage stops for the garment to be tested.

Correct positioning of the carriage, and therefore the garment, can be detected, for example, by microswitches 4 or the like installed along the route; when the said microswitches are activated by the passing of the carriage, they stop the devices that drive the carriages containing the garments forward, and activate the reading and testing devices.

The test area is fitted with a pair of supports 5 and 6 constituted by boards or the like to which a set of colour reference samples 7 and a set of reflectivity measurement samples 8 are applied.

This area also contains two television cameras or similar image digitalisation systems, shown as 9 and 10 in FIG. 2, which film the garment and the two boards 5 and 6 bearing the reference samples from the front and back.

The television cameras are preferably the type with solid-state sensors, in particular CCD sensors.

Television cameras 9 and 10 serve to test the colour and reflecting capacity of the bands applied to the garment.

The test area also contains two pairs of lamps 11 and 12, positioned on opposite sides of the garment; one lamp in each pair illuminates the garment and the boards bearing the samples from an angle of approx. 45° (to measure the colour), and the other illuminates them from an angle of approx. 4° (to measure the characteristics of the reflecting bands).

The angles indicated could be different, where required by the standards in force.

The television cameras are connected to a computer which captures the images supplied, processes them and compares the colour and brightness values read for each zone of the garment with the corresponding values of the reference samples illuminated by the same light.

The computer then displays the results on a screen on which the outline of the garment appears, with the parts of the surface found to conform to the standard shown in one colour and the parts of the surface considered non-conforming shown in a different colour.

The program could obviously be written in such a way as to supply an image printed on paper with details of the results, process those results to produce statistics, etc.

An expert in the field could devise numerous modifications and variations, all of which should be deemed to fall within the scope of this invention.

What is claimed is:

1. A method of testing color and reflectivity of high-visibility garments, said method comprising the following steps:

simultaneously acquiring by the same test unit a digitalized image of the garment and a set of reference samples, illuminated by a same light source;

breaking down the image of the garment into a number of zones of limited size;

reading the color and reflectivity values of each of said zones;

comparing said samples, read simultaneously with the garment, and determining an extent to which the values of each of said zones differ from the samples;

displaying an image of the garment showing the zones whose values fall within the normal range in one color, and the zones whose values fall outside the range in a different color.

2. The method of claim 1, wherein the reading is performed simultaneously from the front and back of the garment by means of two separate test units.

3. The method of claim 1 or 2, wherein two separate readings are taken with the garment illuminated by lights originating from different angles to test its color and reflectivity.

4. A unit designed to test the color and reflectivity of high-visibility garments comprising:

systems designed to acquire a digitalized image of the garment and of one or more reference samples positioned close to the said garment;

systems designed to break down the image acquired of the garment into a number of parts of limited size;

systems designed to read the brightness and color of each of said zones of limited size;

systems designed to compare the values read in correspondence with each of said zones with the values read of said reference sample, illuminated by the same light source, simultaneously with the garment;

systems designed to display a color image of the said garment, in which the parts that fail to conform to the standard are displayed in a different color from the others.

5. The test unit of claim 4, characterized in that it includes common light sources designed to illuminate the garment to be tested and the reference samples simultaneously.

6. The test unit of claim 4, wherein further comprising a number of carriages which move along a track, wherein said carriages, with garments hanging from them, pass alongside television cameras designed to acquire a digitalized image of the garments; and lighting devices able to illuminate the garments and the reference samples simultaneously.

* * * * *